(12) United States Patent
Huber et al.

(10) Patent No.: US 10,463,737 B2
(45) Date of Patent: Nov. 5, 2019

(54) SILICONE ACRYLATE COMPOSITIONS AND METHODS OF PREPARING THE SAME

(71) Applicant: Dow Corning Corporation, Midland, MI (US)

(72) Inventors: Robert O Huber, Midland, MI (US); Gary Lee Loubert, Saginaw, MI (US); Gerald K Schalau, II, Freeland, MI (US); Simon Toth, Midland, MI (US)

(73) Assignee: DOW CORNING CORPORATION, Midland, MI (US)

( * ) Notice: Subject to any disclaimer, the term of this patent is extended or adjusted under 35 U.S.C. 154(b) by 0 days.

(21) Appl. No.: 15/532,362

(22) PCT Filed: Jan. 29, 2016

(86) PCT No.: PCT/US2016/015500
§ 371 (c)(1),
(2) Date: Jun. 1, 2017

(87) PCT Pub. No.: WO2016/123418
PCT Pub. Date: Aug. 4, 2016

(65) Prior Publication Data
US 2017/0368179 A1    Dec. 28, 2017

Related U.S. Application Data

(60) Provisional application No. 62/109,415, filed on Jan. 29, 2015.

(51) Int. Cl.
| | |
|---|---|
| *A61K 47/24* | (2006.01) |
| *C08F 130/08* | (2006.01) |
| *C08F 275/00* | (2006.01) |
| *C09J 151/00* | (2006.01) |
| *A61K 9/70* | (2006.01) |
| *C08F 220/18* | (2006.01) |
| *C09J 133/14* | (2006.01) |
| *C08F 230/08* | (2006.01) |

(52) U.S. Cl.
CPC ............ *A61K 47/24* (2013.01); *A61K 9/7061* (2013.01); *C08F 130/08* (2013.01); *C08F 220/18* (2013.01); *C08F 230/08* (2013.01); *C08F 275/00* (2013.01); *C09J 133/14* (2013.01); *C09J 151/00* (2013.01)

(58) Field of Classification Search
CPC ..................................................... C08L 33/10
See application file for complete search history.

(56) References Cited

U.S. PATENT DOCUMENTS

| | | | |
|---|---|---|---|
| 4,766,185 A | 8/1988 | Ryntz et al. | |
| 4,873,298 A | 10/1989 | Ryntz | |
| 5,288,827 A | 2/1994 | Li et al. | |
| 5,308,887 A | 5/1994 | Ko et al. | |
| 5,461,134 A | 10/1995 | Leir et al. | |
| 5,474,783 A | 12/1995 | Miranda et al. | |
| RE35,474 E * | 3/1997 | Woodard ............. | A61K 9/7069 424/448 |
| 6,469,119 B2 | 10/2002 | Basil et al. | |
| 6,828,404 B2 | 12/2004 | Crivello | |
| 7,026,424 B2 | 4/2006 | Schafer et al. | |
| 7,517,928 B2 | 4/2009 | Bender et al. | |
| 8,124,689 B2 | 2/2012 | Loubert et al. | |
| 8,580,891 B2 | 11/2013 | Liu et al. | |
| 8,703,175 B2 | 4/2014 | Kanios et al. | |
| 2009/0196911 A1 | 8/2009 | Loubert et al. | |
| 2012/0095159 A1* | 4/2012 | Liu ....................... | C08F 220/18 524/588 |
| 2012/0108560 A1 | 5/2012 | Evans et al. | |
| 2014/0276479 A1* | 9/2014 | Nguyen ............... | A61K 31/565 604/290 |

FOREIGN PATENT DOCUMENTS

| | | |
|---|---|---|
| EP | 0380236 | 5/1995 |
| EP | 1076081 | 2/2001 |
| WO | WO2006003032 | 1/2006 |
| WO | 2007050580 | 5/2007 |
| WO | WO2010124187 | 10/2010 |

OTHER PUBLICATIONS

Hui Li et al: "One-step fabrication of a superhydrophobic polymer surface from an acrylic copolymer containing POSS by spraying", RSC Advances: an international journal to further the chemical sciences, vol. 4, No. 107, Jan. 1, 2014 (Jan. 1, 2014), pp. 62694-62697.

* cited by examiner

*Primary Examiner* — Kuo Liang Peng
(74) *Attorney, Agent, or Firm* — Matthew T. Fewkes (57) ABSTRACT

Silicone acrylate copolymer composition, namely, silicone resin-acrylate copolymers and methods of preparing the same. The silicone acrylate composition may include a silicone resin coupled with an acrylate polymer via a linking group. The silicone acrylate composition may be formed by preparing an acrylate or a (meth)acrylate functional resin and carrying out acrylate polymerization in the presence of a functionalized resin. A silane-functional acrylate polymer may be prepared, followed by a reaction to couple a resin to the silane-functional acrylate polymer. The resulting copolymer may then be used as desired, e.g., added to a silicone and acrylate mixture to create a non-separating blend.

9 Claims, 1 Drawing Sheet

SILICONE ACRYLATE COMPOSITIONS AND METHODS OF PREPARING THE SAME

CROSS REFERENCE TO RELATED APPLICATIONS

This application is a U.S. national stage filing under 35 U.S.C. § 371 of PCT Application No. PCT/US16/015500 filed on 29 Jan. 2016, currently pending, which claims the benefit of U.S. Provisional Patent Application No. 62/109,415 filed 29 Jan. 2015 under 35 U.S.C. § 119 (e). PCT Application No. PCT/US16/015500 and U.S. Provisional Patent Application No. 62/109,415 are hereby incorporated by reference.

BRIEF SUMMARY OF THE INVENTION

The embodiments described herein relate to silicone acrylate copolymer compositions. More specifically, the embodiments described herein relate to silicone resin-acrylate copolymers and methods of preparing the same.

BRIEF DESCRIPTION OF THE DRAWINGS

Various advantages of the invention will become apparent upon reading the following detailed description and upon reference to the drawings.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF THE INVENTION

The embodiments described herein are directed toward silicone acrylate copolymer compositions and methods of preparing the same. The silicone acrylate compositions may be used in a variety of applications, including pressure sensitive adhesives (PSAs), film formers, PSA additives, as compatibilizing agents for assisting in creating stable, non-separating silicone and acrylic adhesive blends, and the like. The silicone acrylate copolymer compositions may generally be used alone or in wide ranges of mixing ratios and addition levels with PSAs to act as a PSA, film former, PSA additive, and/or compatibilizing agent. Blends of silicone pressure sensitive adhesives (PSAs) and acrylic polymers in a transdermal drug delivery system may assist in optimizing the solubility of an active agent, thereby creating a system with increased drug delivery efficiency. However, because the blends are generally thermodynamically unstable, undesirable gross phase separation typically occurs upon drying of the adhesives.

According to one embodiment, a silicone acrylate composition includes a silicone resin coupled with an acrylate polymer via a linking group. The silicone acrylate composition may be formed by preparing an acrylate or a (meth) acrylate functional resin and carrying out acrylate polymerization in the presence of a functionalized resin. In another embodiment, a silane-functional acrylate polymer may be prepared, followed by a reaction to couple a resin to the silane-functional acrylate polymer. The resulting copolymer may then be used as desired, e.g., added to a silicone and acrylate mixture to create a non-separating blend.

According to one embodiment, a silicone acrylate composition has a general formula as follows:

Each $R^1$ is independently selected from hydrogen or methyl, and each $R^2$ and $R^3$ is independently selected from hydrogen, hydrogen alkyls, branched alkyls, methyl, ethyl, propyl, n-butyl, iso-butyl, tert-butyl, hexyl, 2-ethylhexyl, iso-octyl, iso-nonyl, iso-pentyl, tridecyl, stearyl, lauryl, hydroxyethyl acetate, (hydroxyethyl)methacrylate, methacrylate esters, acrylate esters, and any combination thereof. Each $R^4$ is a silane having the general formula wherein $R^5$ is selected from —$(CH_2)_2$—, —$(CH_2)_3$—NH—C(=O)—O—$CH_2$—$CH_2$—, —$(CH_2)_3$—NH—$CH_2$—CH(OH)—$CH_2$—, and —$OCH_2$—$CH_2$—, and each $R^6$, $R^7$, and $R^8$ is independently selected from C1-C12 alkyl, —O—(Si—O)p-Si$(CH_3)_3$ where p is from 0-1000, phenyl, and —$(CH_2)_n$—CH=$CH_2$ where n is between 0 and 6. $R^4$ of Formula I or Formula II may have the formula The silicone acrylate composition of Formula I or Formula II may include between about 0-99% w/w x groups, between about 0-99% w/w y groups, between about 0-20% w/w s groups, and between about 1-80% w/w r groups. The % w/w of at least one of the x groups and the y groups is not zero.

Each R of Formula I or Formula II may be a silsesquioxane having the general formula $[(R^9)_2R^{10}SiO_{1/2}]_a$ $[SiO_{4/2}]_q[R^{11}SiO_{3/2}]_t[(R^{12})_3SiO_{1/2}]_m$, where $R^9$ is selected from C1-C12 alkyl, —O—(Si—O)p-Si(CH$_3$)$_3$ where p is from 0-200, phenyl, and —(CH$_2$)$_n$—CH=CH$_2$ where n is between 0 and 6. R$^{10}$ is selected from —(CH$_2$)$_2$—, —(CH$_2$)$_3$—NH—C(=O)—O—CH$_2$—CH$_2$—, —(CH$_2$)$_3$—NH—CH$_2$—CH(OH)—CH$_2$—, and —OCH$_2$—CH$_2$—. R$^{10}$ is selected from acrylate functional silanes, acrylate functional silazanes, acrylate functional disilazanes, acrylate functional disiloxanes, methacrylate functional silanes, methacrylate functional silazanes, methacrylate functional disilazanes, methacrylate functional disiloxanes, and any combination(s) thereof. R$^{11}$ is selected from phenyl, C1-C12 alkyl, —OH, isopropoxy, —(CH$_2$)$_n$—CH=CH$_2$ where n is between 0 and 6. R$^{12}$ is selected from C1-C12 alkyl. In one embodiment, a is from 1 to 5 per R unit, q is from 1 to 300, t is from 0-300, m is from 4-300, and the ratio of m/q is between about 10/90 to about 90/10. In one embodiment, a is 1.

According to another embodiment, a thermodynamically stable silicone acrylate blend composition includes (a) a silicone acrylate composition of Formula I or Formula II; (b) a silicone PSA; and (c) an acrylic polymer. The silicone acrylate blend composition lacks covalent bonds between the silicone acrylate copolymer and the silicone PSA or the acrylic polymer. The silicone PSA may be selected from amine-compatible silicone adhesives and any combination(s) thereof. In one non-limiting embodiment, the silicone PSA has the general formula [SiO$_{4/2}$]$_g$[R$^{13}$SiO$_{3/2}$]$_h$[(R$^{14}$)$_3$SiO$_{1/2}$]$_i$[(R$^{14}$)$_3$SiO$_{2/2}$]$_d$, wherein R$^{13}$ is —OH, isopropoxy, or the combination(s) thereof, and R$^{14}$ is C1-C12 alkyl. In one embodiment, g may be between about 5-50 mol %, h may be between about 0.1-20 mol %, i may be between about 5-50 mol %, d may be between about 5-90%, and the weight ratio of (g+h+i)/d may be between about 10/90 to about 90/10.

According to another embodiment, a thermodynamically stable silicone acrylate blend composition includes (a) a silicone acrylate composition of Formula I or Formula II, and (b) a silicone PSA. The silicone acrylate blend composition lacks covalent bonds between the silicone acrylate composition and the silicone PSA. The silicone PSA may be selected from amine-compatible silicone adhesives and any combination(s) thereof. The silicone PSA may have the general formula [SiO$_{4/2}$]$_g$[R$^{13}$SiO$_{3/2}$]$_h$[(R$^{14}$)$_3$SiO$_{1/2}$]$_i$[(R$^{14}$)$_3$SiO$_{2/2}$]$_d$, wherein R$^{13}$ is —OH, isopropoxy, or the combination(s) thereof, and R$^{14}$ is C1-C12 alkyl. In one embodiment, g may be between about 5-50 mol %, h may be between about 0.1-20 mol %, i may be between about 5-50 mol %, d may be between about 5-90%, and the weight ratio of (g+h+i)/d may be between about 10/90 to about 90/10.

The methods described herein may incorporate the use of any suitable types of catalysts or combination(s) thereof. The catalyst(s) may be selected from peroxide, azo compounds, 2,2'-azobis(2-methylbutyronitrile), alkyl borane catalysts, any combination(s) thereof, and the like. If the catalyst is an alkyl borane catalyst, the preparation of the acrylic polymer may take place at ambient conditions. If the catalyst is a peroxide or azo compound, the preparation of the silicone acrylic composition may take place at an elevated temperature of between above room temperature and about 100° C.

The silicone PSA of the embodiments described herein may be silanol-functional or capped with hexamethyldisilazane. Alternatively, the PSA may include those described in U.S. Pat. No. 4,655,767, which is incorporated by reference herein. Specifically, the PSA may include a blend of a chemically-treated silicone PSA composition with less than about 30 wt % based on nonvolatile solids content of a chemically-treated modifier comprising from 1 to 100 parts by weight of a silicone resin copolymer consisting essentially of R$_3$ SiO$_{1/2}$ units and SiO$_{4/2}$ units in a mole ratio of from 0.6 to 0.9 R$_3$ SiO$_{1/2}$ units for each SiO$_{4/2}$ unit present and from 0 to 99 parts by weight of at least one polydiorganosiloxane consisting essentially of ARSiO units terminated with endblocking TRASiO$_{1/2}$ units, each said polydiorganosiloxane having a viscosity of from 100 centipoise to 30,000,000 centipoise at 25° C.

The acrylic polymer of the embodiments described herein may be an acrylic polymer compound selected from aliphatic acrylates, aliphatic methacrylates, cycloaliphatic acrylates, cycloaliphatic methacrylates, acrylam ides, methacrylam ides, hydroxy-functional (meth)acrylates, carboxy-functional (meth)acrylates, and any combination(s) thereof. Each of the acrylic polymer compounds may have up to 20 carbon atoms in the alkyl radical. The aliphatic acrylates may be selected from methyl acrylate (MA), ethyl acrylate, propyl acrylate, n-butyl acrylate, iso-butyl acrylate, tert-butyl acrylate, hexyl acrylate, 2-ethylhexyl acrylate (EHA), iso-octyl acrylate, iso-nonyl acrylate, iso-pentyl acrylate, tridecyl acrylate, stearyl acrylate, lauryl acrylate, and any combination(s) thereof. The aliphatic methacrylates may be selected from methyl methacrylate, ethyl methacrylate, propyl methacrylate, n-butyl methacrylate, iso-butyl methacrylate, tert-butyl methacrylate, hexyl methacrylate, 2-ethylhexyl methacrylate, iso-octyl methacrylate, iso-nonyl methacrylate, iso-pentyl methacrylate, tridecyl methacrylate, stearyl methacrylate, lauryl methacrylate, acrylam ides, may be selected from methyl acrylamide, ethyl acrylamide, propyl acrylamide, isopropyl acrylamide n-butyl acrylamide, iso-butyl acrylamide, tert-butyl acrylamide, hexyl acrylamide, 2-ethylhexyl acrylamide, iso-octyl acrylamide, iso-nonyl acrylamide, iso-pentyl acrylamide, tridecyl acrylamide, stearyl acrylamide, lauryl acrylamide, and any combination(s) thereof. methacrylamides, may be selected from methyl methacrylamide, ethyl methacrylamide, propyl methacrylamide, isopropyl methacrylamide, n-butyl methacrylamide, iso-butyl methacrylamide, tert-butyl methacrylamide, hexyl methacrylamide, 2-ethylhexyl methacrylamide, iso-octyl methacrylamide, iso-nonyl methacrylamide, iso-pentyl methacrylamide, tridecyl methacrylamide, stearyl methacrylamide, lauryl methacrylamide, hydroxy-functional (meth)acrylates, carboxy-functional (meth)acrylates and any combination(s) thereof.

A transdermal drug delivery system, according to one embodiment, may include a silicone acrylate composition of the embodiments described herein and an active agent for controlled transdermal delivery to a substrate. The transdermal drug delivery system may optionally include penetration enhancers and/or polymers configured to prevent crystallization of the active agent.

In addition to active agent and silicone-based excipients, various excipients and/or enhancing agents may be incorporated into the topical formulation. As generally understood by those skilled in the art, excipients are additives that are used to convert the active agent into appropriate dosage forms that are suitable for application to the substrate. Excipients may also be added to stabilize the formulation and to optimize application characteristics, such as flowability.

Examples of potential excipients include, but are not limited to, excipients that are found in the Cosmetics, Toiletry, Fragrance Association (CTFA) ingredient Database and the handbook of pharmaceutical excipients such as absorbents, anticaking agents, antioxidants (such as, ascorbic acid, ascorbic acid polypeptide, ascorbyl dipalmitate, BHA, BHT, magnesium ascorbate, magnesium ascorbyl phosphate, propyl gallate sodium ascorbate, sodium ascorbyl/cholesteryl phosphate, sodium bisulfite, sodium erythorbate, sodium metabisulfide, tocopheryl acetate, tocopheryl nicotinate), antistatic agents, astringents, binders, buffering agents, bulking agents, chelating agents, colorants, cosmetic astringents, biocides (such as parabens, organic acids, organic bases, alcohols isothiazolinones and others), deodorant agents, emollients, external analgesics (such as Benzyl Alcohol, Methyl Salicylate, Camphor, Phenol, Capsaicin, Juniper Tar (Menthol, Resorcinol, Methyl Nicotinate, and Turpentine Oil), film formers, flavoring agents, fragrance ingredients, humectants, lytic agents, moisturizing agents, occlusivity enhancers, opacifying agents, oxidizing agents (such as Peroxides, Bromates, Chlorates, Potassium Iodates, and Persulfates), reducing agents (such as Sulfites, Thioglycolates, Cystein, Cysteine HCl, Glutathione, Hydroquinone, Mercaptopropionic Acid, Sulfonates, Thioglycolic Acid), penetration enhancers, pesticides, plasticizers, preservatives, skin bleaching agents such as hydroquinone, skin conditioning agents, skin protectants (such as Allantoin, Aluminum Acetate, Dimethicone, Glycerin, Kaolin, Lanolin, Mineral Oil, Petrolatum, Talc, and Zinc Oxide), slip modifiers, solubilizing agents, solvents, sunscreen agents (such as Aminobenzoic Acid, Cinoxate, cinnamates, Aminobenzoates, Oxybenzone, Red Petrolatum, Titanium Dioxide, and Trolamine Salicylate), surface modifiers, surfactants and emulsifying agents, suspending agents, thickening agents, viscosity controlling agents including increasing or decreasing agents, UV light absorbing agents (such as Acetaminosalol, Allatoin PABA, Benzalphthalide, and Benzophenone). Other possible excipients include, but are not limited to, sugars and derivatives (such as acacia, dextrin, dextrose, maltodextrin, and sorbitol), starch derivatives, cellulosic materials (such as methyl cellulose, Ethylcellulose, Hydroxyethylcellulose, Hydroxypropylcellulose, and Hydroxypropylmethylcellulose), polysaccharides (such as dextrates, guar gum, and xanthan gum), polyethers, suspending agents cyclodextrins, and others.

Enhancers may also be exemplified by monohydric alcohols such as ethanol and isopropyl, butyl and benzyl alcohols, or dihydric alcohols such as ethylene glycol, diethylene glycol, or propylene glycol, dipropylene glycol and trimethylene glycol, or polyhydric alcohols such as butylene glycol, hexylene glycol, polypropylene glycol, ethylene glycol, and polyethylene glycol, which enhance drug solubility; polyethylene glycol ethers of aliphatic alcohols (such as cetyl, lauryl, oleyl and stearyl) including polyoxyethylene (4) lauryl ether, polyoxyethylene (2) oleyl ether and polyoxyethylene (10) oleyl ether commercially available under the trademark BRIJ® 30, 93 and 97, respectively, from Uniqema Americas LLC (Wilmington, Del.), and others such as BRIJ® 35, 52, 56, 58, 72, 76, 78, 92, 96, 700 and 721; vegetable, animal and fish fats and oils such as olive, and castor oils, squalene, lanolin; fatty acids such as oleic, linoleic, and capric acid, and the like; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability; salicylic acid; amino acids; benzyl nicotinate; and higher molecular weight aliphatic surfactants such as lauryl sulfate salts; and esters of sorbitol and sorbitol anhydride such as polysorbate 20 commercially available under the trademark Tween® 20 from Uniqema Americas LLC (Wilmington, Del.), as well as other polysorbates such as 21, 40, 60, 61, 65, 80, 81, and 85. Other enhancers include enzymes, panthenol, and other non-toxic enhancers commonly used in transdermal or transmucosal compositions.

Polyhydric alcohols also include glycols, triols and polyols having 4 to 6 alcoholic hydroxyl groups. Typical of said glycols are glycols containing 2 to 6 carbon atoms, e.g. ethylene glycol, propylene glycol, butylene glycol, polyethylene glycol (average molecular weight about 200-8,000, preferably about 200 to 6,000), etc. Examples of said triols include glycerin, trimethylolpropane, etc. Said polyols are exemplified by sorbitol, polyvinylpyrrolidone, etc. These polyhydric alcohols may be used either singularly or in combination (preferably, of two or three). Thus, for example, glycerin or dipropylene glycol alone, or a mixture of either glycerin or dipropylene glycol with butylene glycol can be employed.

EXAMPLES

The following examples are intended to illustrate the invention to one of ordinary skill in the art and should not be interpreted as limiting the scope of the invention set forth in the claims.

Example 1: Preparation of Methacrylate Functional Resin

About 150 g of a resin composition including about 79% in xylene solution, about 0.076 g of water, and about 0.48 g of 3-methacryloxypropyldimethylchlorosilane (from Gelest Inc., Morrisville, Pa.) was added to a 16-ounce glass jar. The jar was placed on a rotating wheel to mix for about 20 hours. After about 20 hours, the reaction mixture was analyzed by $^1$H NMR, which revealed that more than 99% of chlorosilane was reacted off, indicating that the reaction generated HCl. Accordingly, about 0.92 g of sodium bicarbonate was added to the reaction mixture to neutralize the HCl. After neutralization, the product was filtered through Whatman #2 filter paper in a pressure filter. Xylene was then removed with stripping under full vacuum, followed by drying in a hood at or about room temperature. About 99.12 g of white crystalline product was obtained, which was then dissolved in about 79.1 g of ethyl acetate (from Acros Organics, Geel, Belgium).

The resulting methacryloxypropyl functionalized resin was the precursor/intermediate used to prepare the silicone acrylate composition of Example 2 below.

Example 2: Preparation of a Silicone Acrylate Composition

In an 8-ounce jar, a mixture of the following was prepared: about 31.44 g of 2-EHA (from Sigma-Aldrich, St. Louis, Mo.), about 31.44 g of MA (from Sigma-Aldrich), about 51.37 g of the methacryloxypropyl functionalized resin from Example 1, and about 0.091 g of 2,2'azobis-(2-methylbutyronitrile) (from DuPont, Wilmington, Del.). About 85.76 g of the resulting mixture was added to a pear-shaped vessel. The rest of the mix, along with about 102.74 g of ethyl acetate solvent (from Acros Organics), was added to a previously $N_2$-inerted 3-neck round bottom flask equipped with a stirrer, condenser, and temperature controller. The content of the 3-neck flask then was heated to the reflux temperature of ethyl acetate (about 77° C.) and held for about one hour. Next, over an about three hour period, the content of the pear-shaped vessel was added to the 3-neck flask while keeping the reaction temperature at or near solvent reflux. The reaction mixture was held at or near reflux temperature for another about 20 hours. The reaction mixture was then cooled to about room temperature. About 200 g of the resulting reaction mixture was added slowly to about 200 g of isopropyl alcohol (IPA). The precipitated material was then separated and dried. About 70 g of the dried material was then added to ethyl acetate to make an about 42% solution.

Comparative Example 3: Blend of Acrylate Polymer and Silicone PSA Preparation

In an 8-ounce jar, a mixture of the following was prepared: about 31.5 g of 2-EHA (from Sigma-Aldrich), about 31.5 g of MA (from Sigma-Aldrich), about 106.5 g of a silicone adhesive (about 60% ethyl acetate solution), and about 0.091 g of 2,2'azobis-(2-methylbutyronitrile) (from DuPont). About 124.8 g of the resulting mixture was added to a pear-shaped vessel. The rest of the mixture, along with about 126.8 g of ethyl acetate solvent (from Acros Organics), was added to a previously $N_2$-inerted 3-neck flask equipped with a stirrer, condenser, and temperature controller. The content of the 3-neck flask was then heated to the reflux temperature of ethyl acetate (about 77° C.) and held for about one hour. Next, over an about three hour period, the content of the pear-shaped vessel was added to the 3-neck flask while keeping the reaction temperature at or near solvent reflux. The reaction mixture was held at or near reflux temperature for another about 20 hours. The reaction mixture was then cooled to about room temperature.

The reaction mixture was found to separate upon storage, thereby demonstrating that silicone and acrylate adhesive blends generally undergo phase separation when the two components are not compatibilized and/or when they are not covalently linked together. The separation generally occurs even if the acrylate adhesive is prepared in the presence of the silicone adhesive, as described in this example.

Example 4: Addition of Silicone Acrylate Material

About 1.4 g of the silicone acrylate composition of Example 2 and about 20 g of a blend of acrylate polymer and silicone bio-PSA from Example 3 was thoroughly mixed. The result was a compatibilized blend where the silicone and acrylate components did not separate upon storage or centrifuging.

Comparative Example 5: Preparation of Methacrylate Functional Silicone Bio-PSA 150 g of a silicone adhesive including about 60% in ethyl acetate solution, about 0.14 g of water, and about 0.90 g of 3-methacryloxypropyldimethylchlorosilane (from Gelest Inc.) was added to a 16-ounce glass jar. The jar was placed on a rotating wheel to mix for about 20 hours. After about 20 hours, the reaction mixture was analyzed by $^1$H NMR, which revealed that more than 99% of chlorosilane was reacted off, indicating that the reaction generated HCl. Accordingly, about 1.72 g of sodium bicarbonate was added to the reaction mixture to neutralize the HCl. After neutralization, the product was filtered through Whatman #2 filter paper in a pressure filter. This resulting methacrylate functional silicone bio-PSA was the intermediate used in Comparative Example 6.

Comparative Example 6: Preparation of Silicone Acrylate Co-Reacted Adhesive

In an 8-ounce jar, a mixture of the following was prepared: about 31.5 g of 2-EHA (from Sigma-Aldrich), about 31.5 g of MA (from Sigma-Aldrich), about 100 g of methacrylate functional silicone bio-PSA from Example 5 (about 63% ethyl acetate solution), about 14.55 g of ethyl acetate, and about 0.091 g of 2,2'azobis-(2-methylbutyronitrile) (from DuPont). About 133.23 g of the resulting mixture was added to a pear-shaped vessel. The rest of the mixture from the 8-ounce jar, along with about 122.45 g of ethyl acetate solvent (from Acros Organics), was added to a previously $N_2$-inerted 3-neck flask equipped with a stirrer, condenser, and temperature controller. The content of the 3-neck flask then was heated to the reflux temperature of ethyl acetate (about 77° C.) and held for about one hour. Next, over an about three-hour period, the contents of the pear-shaped vessel were added to the 3-neck flask while keeping the reaction temperature at or near solvent reflux. The reaction mixture was held at or near reflux temperature for another about 20 hours. The reaction mixture was cooled to about room temperature. The covalent bond formation between the acrylate and silicone phase in the reaction mixture assists in preventing the separation of the silicone and acrylate phases.

Example 7: Centrifuge Test

Centrifuge tubes were filled with materials formed in Example 3, Example 4, and Example 6. All were centrifuged at about 4000 rpm for about 30 minutes in a Sorvall™ ST40 centrifuge (Thermo Scientific, Rochester, N.Y.). Centrifuge testing was used to accelerate the effect of gravity upon storage. The results are compared in the table below.

TABLE 1

| | Comparative Ex. 3 | Ex. 4 | Comparative Ex. 6 |
|---|---|---|---|
| Before Centrifuge | Uniformly opaque | Uniformly opaque | Uniformly opaque |
| After Centrifuge | Separate layers of clear material | Uniformly opaque | Uniformly opaque |

Silicone and acrylate adhesives are generally immiscible, and blending them generally results in a thermodynamically unstable mixture that will separate upon storage. The immiscible natures of silicone and acrylate adhesives are indicated by the opaque (as opposed to clear) appearance of the mixture in solvent solution. The results detailed in Table 1 indicate that the immiscible mixture may be stabilized by co-reacting silicone and acrylate adhesive, thereby forming covalent bonds between the two components, as in Comparative Example 6. The immiscible mixture may also be stabilized by adding a compatibilizer (e.g., a silicone acrylate composition) to the mixture, as shown in Example 4. The effectiveness of covalent bonds and compatibilizers is demonstrated by the fact that, after centrifuge treatment (which simulates accelerated storage), the mixture remains uniformly opaque, indicating no or minimal change/separation. The same centrifuge treatment caused the silicone acrylate blend without compatibilizer or covalent bond between the two components to separate, as indicated by the layers of clear materials comprised of the silicone and acrylate components, respectively.

The following examples demonstrate the use of resin-acrylate copolymer compositions as PSAs. Also, the potential use in transdermal drug delivery is demonstrated through the loading and release of estradiol from the materials of the following examples.

Example 8: Preparation of Methacrylate Functional Resin (about 0.28 wt % 3-methacryloxypropyldimethylchlorosilane)

About 200 g of a silicone resin at about 72% solids in xylene and about 100 µL DI water were added to a 500 mL 3-neck flask equipped with an overhead mixer and a dry $N_2$ inlet and were allowed to mix for approximately 30 minutes, after which about 0.41 g 3-methacryloxypropyldimethylchlorosilane (from Gelest Inc.) was added via a syringe. After approximately 24 hours, the solution was neutralized with about 0.77 g sodium bicarbonate and filtered through Whatman #2 filter paper in a pressure filter. Xylene was then removed with stripping under full vacuum, followed by drying in a hood at room temperature. About 134.0 g of white crystalline product was obtained, which was then dissolved in about 57.4 g of ethyl acetate (from Acros Organics). $^1$H NMR confirmed hydrolysis of the chlorosilane and condensation with the resin, resulting in a methacryloxypropyl-functionalized resin.

Example 9: Preparation of Methacrylate Functional Resin (about 0.54 wt % 3-methacryloxypropyldimethylchlorosilane)

About 200 g of a silicone resin at about 72% solids in xylene and about 100 µL DI water were added to a 500 mL 3-neck flask equipped with an overhead mixer and a dry $N_2$ inlet and were allowed to mix for approximately 30 minutes, after which about 0.78 g 3-methacryloxypropyldimethylchlorosilane (from Gelest Inc.) was added via a syringe. After approximately 24 hours, the solution was neutralized with about 1.5 g sodium bicarbonate. After stripping the xylene, about 135.0 g of white crystalline product was obtained, which was then dissolved in about 58.0 g of ethyl acetate (from Acros Organics). $^1$H NMR confirmed hydrolysis of the chlorosilane and condensation with the resin, resulting in a methacryloxypropyl-functionalized resin.

Example 10: Preparation of Methacrylate Functional Resin (about 0.81 wt % 3-methacryloxypropyldimethylchlorosilane)

About 200 g of a silicone resin at about 72% solids in xylene and about 100 µL DI water were added to a 500 mL 3-neck flask equipped with an overhead mixer and a dry $N_2$ inlet and were allowed to mix for approximately 30 minutes, after which about 1.18 g 3-methacryloxypropyldimethylchlorosilane (from Gelest Inc.) was added via a syringe. After approximately 24 hours the solution was neutralized with about 2.4 g sodium bicarbonate. After stripping the xylene, about 126.9 g of white crystalline product was obtained, which was then dissolved in about 54.3 g of ethyl acetate (from Acros Organics). $^1$H NMR confirmed hydrolysis of the chlorosilane and condensation with the resin, resulting in a methacryloxypropyl-functionalized resin.

Example 11: Preparation of Methacrylate Functional Resin (about 1.1 wt % 3-methacryloxypropyldimethylchlorosilane)

About 200 g of a silicone resin at about 72% solids in xylene and about 100 µL DI water were added to a 500 mL 3-neck flask equipped with an overhead mixer and a dry $N_2$ inlet and were allowed to mix for approximately 30 minutes, after which about 1.59 g 3-methacryloxypropyldimethylchlorosilane (from Gelest Inc.) was added via a syringe. After approximately 24 hours, the solution was neutralized with about 3.1 g sodium bicarbonate. After stripping the xylene, about 130.2 g of white crystalline product was obtained, which was then dissolved in about 55.8 g of ethyl acetate (from Acros Organics). $^1$H NMR confirmed hydrolysis of the chlorosilane and condensation with the resin, resulting in a methacryloxypropyl-functionalized resin.

Table 2 below shows the composition analysis, as measured by NMR, of Examples 1, 5, and 8-11.

TABLE 2

| | Protons indicating the presence of components, integral*** | | | |
|---|---|---|---|---|
| Examples | Total methacrylate silane<br>H(1), broad, δ** = 6.11 ppm | Methacrylate silane resin<br>CH3, broad, δ** = 1.94 ppm | Trimethylsilyl of silicone resin* (M)<br>CH3, broad, δ** = 0.12-0.15 ppm | Dimethylsilyl of silicone polymer (D)<br>CH3, broad, δ** = 0.08 ppm |
| Example 1 | 1.8 | 5 | 6500 | n/a |
| Example 5 | 7.31 | 2.8 | 6515 | 5160 |
| Example 8 | 0.19 | 0.62 | 1000 | n/a |
| Example 9 | 0.39 | 1.16 | 1000 | n/a |
| Example 10 | 0.58 | 1.68 | 1000 | n/a |
| Example 11 | 0.78 | 2.35 | 1000 | n/a |

*The weight ratio of M to Q + TOZ was 1.0 (determined by 29Si-NMR)
**Reference shift CHCl3, δ = 7.27 ppm
***Arbitrary number chosen for largest integral as reference

Example 12: Preparation of a Silicone Acrylate Composition from the Methacryloxypropyl-Functionalized Resin of Example 8

About 37.77 g 2-EHA, about 25.23 g MA, about 30.96 g of the methacryloxypropyl-functionalized resin from Example 8, about 7.25 g ethyl acetate, and about 0.091 g 2,2'azobis-(2-methylbutyronitrile) were added to a 16 oz glass jar and mixed to form a pre-reaction mixture. About 75.9 g of the pre-reaction mixture was added to a 250 mL pear-shaped flask. The rest of the pre-reaction mixture, along with about 102.74 g of ethyl acetate solvent (from Acros Organics), was added to a previously $N_2$-inerted 3-neck round bottom flask equipped with a stirrer, condenser, and temperature controller. The content of the 3-neck flask then was heated to the reflux temperature of ethyl acetate (about 77° C.) and held for about one hour. Next, over an about three hour period, the content of the pear-shaped vessel was added to the 3-neck flask while maintaining the reaction temperature at or near solvent reflux. The reaction mixture was held at or near reflux temperature for another about 20 hours. The resulting reaction mixture was then cooled to about room temperature. $^1$H NMR confirmed the final composition, which is provided in Table 3 below. Approximately 3 g of the resulting reaction mixture was added slowly to about 20 g of methanol. The container was vigorously shaken, and the polymer precipitated from the solution. The precipitated material was then separated and dried. $^1$H NMR confirmed the composition of the precipitated material (see Table 3).

Example 13: Preparation of a Silicone Acrylate Composition from the Methacryloxypropyl-Functionalized Resin of Example 9

About 37.85 g 2-EHA, about 25.24 g MA, about 30.89 g of the methacryloxypropyl-functionalized resin from Example 9, about 7.44 g ethyl acetate, and about 0.087 g 2,2'azobis-(2-methylbutyronitrile) were added to a 16 oz glass jar and mixed to form a pre-reaction mixture. About 76.1 g of the pre-reaction mixture was added to a 250 mL pear-shaped flask. The rest of the pre-reaction mixture, along with about 98.8 g of ethyl acetate solvent (from Acros Organics), was added to a previously $N_2$-inerted 3-neck round bottom flask equipped with a stirrer, condenser, and temperature controller. The content of the 3-neck flask then was heated to the reflux temperature of ethyl acetate (about 77° C.) and held for about one hour. Next, over an about three hour period, the content of the pear-shaped vessel was added to the 3-neck flask while maintaining the reaction temperature at or near solvent reflux. The reaction mixture was held at or near reflux temperature for another about 20 hours. The reaction mixture was then cooled to about room temperature. $^1$H NMR confirmed the final composition, which is provided in Table 3 below. Approximately 3 g of the resulting reaction mixture was added slowly to about 20 g of methanol. The container was vigorously shaken, and the polymer precipitated from the solution. The precipitated material was then separated and dried. $^1$H NMR confirmed the composition of the precipitated material (see Table 3).

Example 14: Preparation of a Silicone Acrylate Composition from the Methacryloxypropyl-Functionalized Resin of Example 10

About 37.83 g 2-EHA, about 25.19 g MA, about 31.08 g of the methacryloxypropyl-functionalized resin from Example 10, about 7.21 g ethyl acetate, and about 0.086 g 2,2'azobis-(2-methylbutyronitrile) were added to a 16 oz glass jar and mixed to form a pre-reaction mixture. About 74.8 g of the pre-reaction mixture was added to a 250 mL pear-shaped flask. The rest of the pre-reaction mixture, along with about 98.9 g of ethyl acetate solvent (from Acros Organics), was added to a previously $N_2$-inerted 3-neck round bottom flask equipped with a stirrer, condenser, and temperature controller. The content of the 3-neck flask then was heated to the reflux temperature of ethyl acetate (about 77° C.) and held for about one hour. Next, over an about three hour period, the content of the pear-shaped vessel was added to the 3-neck flask while maintaining the reaction temperature at or near solvent reflux. The reaction mixture was held at or near reflux temperature for another about 20 hours. The reaction mixture was then cooled to about room temperature. $^1$H NMR confirmed the final composition, which is provided in Table 3 below. Approximately 3 g of the resulting reaction mixture was added slowly to about 20 g of methanol. The container was vigorously shaken and the polymer precipitated from the solution. The precipitated material was then separated and dried. $^1$H NMR confirmed the composition of the precipitated material (see Table 3).

Example 15: Preparation of a Silicone Acrylate Composition from the Methacryloxypropyl-Functionalized Resin of Example 11

About 38.02 g 2-EHA, about 25.17 g MA, about 31.04 g of the methacryloxypropyl-functionalized resin from Example 11, about 7.12 g ethyl acetate, and about 0.090 g 2,2'azobis-(2-methylbutyronitrile) were added to a 16 oz glass jar and mixed to form a pre-reaction mixture. About 75.3 g of the pre-reaction mixture was added to a 250 mL pear-shaped flask. The rest of the pre-reaction mixture, along with about 99.3 g of ethyl acetate solvent (from Acros Organics), was added to a previously $N_2$-inerted 3-neck round bottom flask equipped with a stirrer, condenser, and temperature controller. The content of the 3-neck flask then was heated to the reflux temperature of ethyl acetate (about 77° C.) and held for about one hour. Next, over an about three hour period, the content of the pear-shaped vessel was added to the 3-neck flask while maintaining the reaction temperature at or near solvent reflux. The reaction mixture was held at or near reflux temperature for another about 20 hours. The reaction mixture was then cooled to about room temperature. $^1$H NMR confirmed the final composition, which is provided in Table 3 below. Approximately 3 g of the resulting reaction mixture was added slowly to about 20 g of methanol. The container was vigorously shaken and the polymer precipitated from the solution. The precipitated material was then separated and dried. $^1$H NMR confirmed the composition of the precipitated material (see Table 3).

TABLE 3

| Example | Condition | % EHA | % MA | % Silicone Resin | % Residual monomer |
| --- | --- | --- | --- | --- | --- |
| Example 12 | before precipitation | 44.7 | 28.7 | 25.7 | 0.94 |
|  | after precipitation | 52.3 | 34.2 | 13.5 | 0 |
| Example 13 | before precipitation | 44.1 | 28.9 | 25.7 | 1.24 |
|  | after precipitation | 49.8 | 32.4 | 17.8 | 0.09 |

TABLE 3-continued

| Example | Condition | % EHA | % MA | % Silicone Resin | % Residual monomer |
|---|---|---|---|---|---|
| Example 14 | before precipitation | 44.5 | 28.9 | 25.6 | 1 |
|  | after precipitation | 49.1 | 32.1 | 18.8 | 0.07 |
| Example 15 | before precipitation | 40 | 25.6 | 26.7 | 7.48 |
|  | after precipitation | 47.8 | 31 | 20.5 | 0.72 |

Comparative Example 16: Preparation of an Acrylate Composition

About 50.48 g 2-EHA, about 33.70 g MA, about 16.09 g ethyl acetate, and about 0.115 g 2,2'azobis-(2-methylbutyronitrile) were added to a 16 oz glass jar and mixed to form a pre-reaction mixture. About 75.0 g of the pre-reaction mixture was added to a 250 mL pear-shaped flask. The rest of the pre-reaction mixture, along with about 100.0 g of ethyl acetate solvent (from Acros Organics), was added to a previously $N_2$-inerted 3-neck round bottom flask equipped with a stirrer, condenser, and temperature controller. The content of the 3-neck flask then was heated to the reflux temperature of ethyl acetate (about 77° C.) and held for about one hour. Next, over an about three hour period, the content of the pear-shaped vessel was added to the 3-neck flask while keeping the reaction temperature at or near solvent reflux. The reaction mixture was held at or near reflux temperature for another about 20 hours. The reaction mixture was then cooled to about room temperature.

Example 17: Tape Properties of the Compositions of Examples 12-16

The resulting compositions of Examples 12-16 were coated onto both 2 mil and 10 mil polyester using a film applicator and dried for about 5 minutes at room temperature followed by heating for about 5 minutes at about 110° C., resulting in a film thickness of about 1 mil. Static shear was performed by adhering the samples (having an about 1×1 inch contact area) to stainless steel panels. Weights (1 kg) were hung from the samples, and the time to cohesive failure at about room temperature was monitored (using ASTM D3654M and/or PSTC-7). Probe tack testing was performed with a TA Texture Analyzer using a 7 mm, stainless steel punch probe with a 1 inch radius of curvature. Samples were placed under the indexable brass plate to position them for analysis. The following program settings were used: pre-test speed of about 0.5 mm/sec, test speed of about 0.2 mm/sec, post-test speed of about 0.2 mm/sec, test force of about 100 g, dwell time of about 0.5 seconds, trigger force of about 1.0 g, auto trigger mode, and collection rate of about 200 points/second. The average of five measurements is reported in Table 4 below.

TABLE 4

| Sample | Static Shear 2.2 psi, n = 3 (min) | Tack Peak force n = 5 (g) | Tack peak area n = 5 (g.sec) |
|---|---|---|---|
| Example 12 | 162.0 ± 17.7 | 129.1 ± 5.8 | 144.1 ± 9.1 |
| Example 13 | 4085.3 ± 922.1 | 138.5 ± 14.4 | 58.6 ± 13.9 |
| Example 14 | >14,300 | 113.6 ± 18.1 | 39.8 ± 11.9 |

TABLE 4-continued

| Sample | Static Shear 2.2 psi, n = 3 (min) | Tack Peak force n = 5 (g) | Tack peak area n = 5 (g.sec) |
|---|---|---|---|
| Example 15 | >14,300 | 150.2 ± 19.2 | 51.4 ± 12.5 |
| Comparative Example 16 | 38.1 ± 9.4 | 100.8 ± 17.9 | 87.7 ± 24.6 |

These results show that the increase in methacryloxypropyl-functionality on the silicone resin increased the shear properties of the material without substantially influencing the tack. However, with this increase in the cohesive nature of the material, the adhesive failure mechanism is changed, as shown by the decrease in the tack peak area, which indicates reduction in fibrillation. Therefore, the copolymerization of (meth)acrylate-functional silicone resin with (meth)acrylate monomers can be utilized to create resin-acrylate PSA with modified properties over that of acrylic PSA.

Examples 17-21: Estradiol-Loaded Formulations

Example 17 was prepared by adding about 0.3865 g Kollidon K25 PVP and about 0.0774 g estradiol to a scintillation vial. To this, about 0.4650 g ethyl acetate was added to disperse the powders followed by the addition of about 0.2337 g isopropyl alcohol to dissolve the powders. To this solution, about 8.7188 g of the resin-acrylate composition of Example 12, about 0.7501 g of oleic acid/dipropylene glycol (about 1.5:1 w/w), and about 0.897 g ethyl acetate were added and mixed. The scintillation vial was placed on a vial roller and mixed for about 24 hours. After mixing, the formulation was cast onto about 2 mil thick polyester using a film applicator and dried for about 5 minutes at or about room temperature followed by heating for about 5 minutes at about 92° C. to achieve a final coat weight of about 10 mg/cm$^2$. The films were then covered with a fluorocarbon coated release liner. Examples 18-21 were prepared in a similar fashion except that the composition of Example 12 was substituted with the composition of Example 13 for Example 18, the composition of Example 14 for Example 19, the composition of Example 15 for Example 20, the composition of Comparative Example 16 for Comparative Example 20. The components of each of Examples 17-21 are listed in Table 5 below.

TABLE 5

| Materials | Example 17 | Example 18 | Example 19 | Example 20 | Comparative Example 21 |
|---|---|---|---|---|---|
| Kollidon K25 PVP (g) | 0.3865 | 0.3867 | 0.3864 | 0.3866 | 0.3867 |
| Estradiol (g) | 0.0774 | 0.0776 | 0.0777 | 0.0779 | 0.0777 |
| Oleic acid/Dipropylene glycol (1.5:1 w/w) (g) | 0.7501 | 0.7500 | 0.7535 | 0.7509 | 0.7509 |
| Example12 (g) | 8.7188 | — | — | — | — |
| Example 13 (g) | — | 8.6366 | — | — | — |
| Example 14 (g) | — | — | 8.8993 | — | — |
| Example 15 (g) | — | — | — | 9.8866 | — |
| Comparative Example 16 (g) | — | — | — | — | 9.0679 |
| Ethyl Acetate (g) | 1.3620 | 1.9074 | 1.8296 | 0.6635 | 1.3683 |
| Isopropyl alcohol (g) | 0.2337 | 0.2351 | 0.2369 | 0.2406 | 0.2323 |

Example 22: Estradiol Flux

Figure 1:
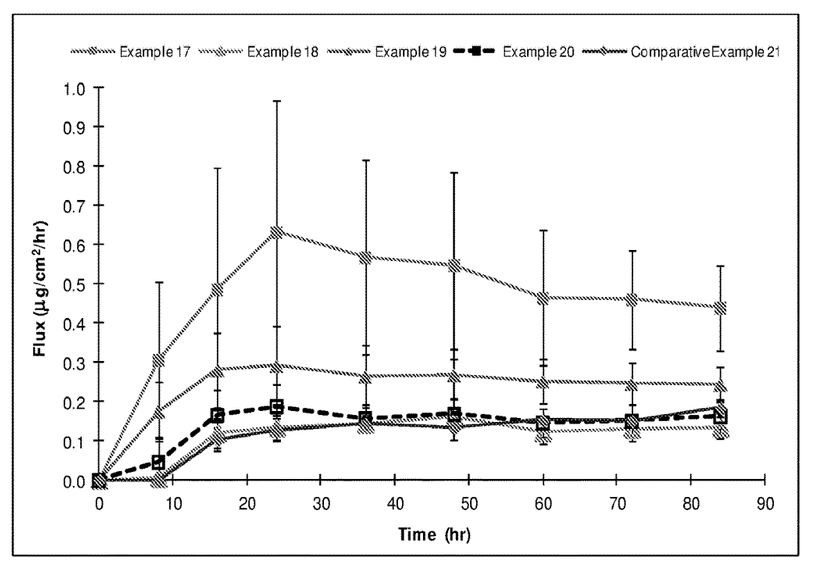
FIG. 1 is a graph showing the estradiol flux of compositions according to embodiments described herein.

Patches having a surface area of about 0.495 cm$^2$ were fluxed (n=3) through heat separated epidermis from full-thickness human cadaver skin. The receptor fluid was phosphate buffered saline having a pH of about 7.4, and the study was conducted at about 32° C. Samples of the receptor fluid were taken at about 8, 16, 24, 36, 48, 60, 72 and 84 hours with full replacement using fresh phosphate buffered saline. Samples were analyzed for estradiol concentration using an appropriate UPLC method, and the results are reported in Table 6 below and in FIG. 1.

TABLE 6

| Sample | Cumulative Release 84 hr, n = 3 (µg/cm$^2$) | Cumulative Release, n = 3 (%) |
| --- | --- | --- |
| Example 17 | 41.14 ± 17.23 | 24.01 ± 10.06 |
| Example 18 | 10.40 ± 1.88 | 7.08 ± 1.28 |
| Example 19 | 21.33 ± 5.64 | 14.91 ± 3.95 |
| Example 20 | 12.64 ± 3.67 | 8.26 ± 2.4 |
| Comparative Example 21 | 11.06 ± 0.58 | 7.09 0.37 |

These results indicate the copolymerization of (meth)acrylate-functional silicone resin with (meth)acrylate monomers can be utilized to create resin-acrylate PSA with modified drug release properties over that of acrylic PSA.

Example 23: Preparation of a Silicone Acrylate Film Former Composition

About 7.5 g methyl methacrylate, about 5 g butyl acrylate, about 7.5 g of the methacryloxypropyl-functionalized resin from Example 9, about 50 g ethyl acetate, and about 0.087 g 2,2'azobis-(2-methylbutyronitrile) were added to a 16 oz glass jar and mixed to form a pre-reaction mixture. The pre-reaction mixture was added to a previously N$_2$-inerted 3-neck round bottom flask equipped with a stirrer, condenser, and temperature controller. About 22.5 g methyl methacrylate, about 15 g Butyl acrylate, about 22.5 g of the methacryloxypropyl-functionalized resin from Example 9, and about 112 g ethyl acetate were added to a 16 oz glass jar and mixed to form a feed mixture. The feed mixture was then transferred to a 250 mL pear-shaped flask. About 17 g of ethyl acetate and about 0.6 g of 2,2'azobis-(2-methylbutyronitrile) were added to a 2 oz glass vial and mixed to form a initiator mixture. The initiator mixture was then transferred to a syringe assembled on a syringe pump. The content of the 3-neck flask then was heated to the reflux temperature of ethyl acetate (about 77° C.) and held for about 15 minutes. Over an about two hour period, the content of the pear-shaped vessel was added to the 3-neck flask while maintaining the reaction temperature at or near solvent reflux. Simultaneously, over an about four hour period, the initiator mixture of the syringe pump was added. The reaction mixture was held at or near reflux temperature for another about 16 hours. The reaction mixture was then cooled to about room temperature. $^1$H NMR confirmed the final composition, which was determined after all volatile components evaporated from the film former: 43.3% polymerized methylmethacrylate, 26.3% polymerized butyl acrylate, and 30.4% silicone resin. The material was cast, the solvent dried, and non-tacky film continuous film formed.

While the invention is susceptible to various modifications and alternative forms, specific embodiments have been shown by way of example in the examples and described in detail herein. It should be understood, however, that the invention is not intended to be limited to the particular forms disclosed. Rather, the invention is to cover all modifications, equivalents, and alternatives falling within the spirit and scope of the invention as defined by the appended claims.

The invention claimed is:

1. A silicone acrylate having a general formula:

wherein
each R$^1$ is independently selected from hydrogen or methyl;
each R$^2$ and R$^3$ is independently selected from hydrogen alkyls, branched alkyls, methyl, ethyl, propyl, n-butyl, iso-butyl, tert-butyl, hexyl, 2-ethylhexyl, iso-octyl, iso-nonyl, iso-pentyl, tridecyl, stearyl, lauryl, and; and
each R$^4$ is a silane having the general formula:

wherein R$^5$ is selected from —(CH$_2$)$_3$—NH—C(=O)—O—CH$_2$—CH$_2$—, —(CH$_2$)$_3$—NH—CH$_2$—CH(OH)—CH$_2$—, and —OCH$_2$—CH$_2$—, and each R$^6$, R$^7$, and R$^8$ is independently selected from C1-C12 alkyl, phenyl, and —(CH$_2$)$_n$—CH=CH$_2$ where n is from 0 to 6, or and wherein each R is a silsesquioxane having the general formula:

$$[(R^9)_2R^{10}SiO_{1/2}]_a[SiO_{4/2}]_q[R^{11}SiO_{3/2}]_t[(R^{12})_3SiO_{1/2}]_m,$$

wherein R$^9$ is C1-12 alkyl, R$^{10}$ is —(CH$_2$)$_z$—, where z is 3, R$^{11}$ is selected from phenyl, C1-C12 alkyl, —OH, isopropoxy, and —(CH$_2$)$_n$—CH=CH$_2$, where n is between 0 and 6, and R$^{12}$ is selected from C1-C12 alkyl, wherein a is from 1 to 5 per R unit, q is from 1 to 300, t is 0, m is from 4-300, and the ratio of m/q is between 10/90 to 90/10,
wherein the silicone acrylate includes between 0-99% w/w x groups, between 0-99% w/w y groups, 0% w/w s groups, and between 1-80% w/w r groups, where the % w/w of at least one of the x groups and the y groups is not zero.

2. A thermodynamically stable silicone acrylate blend comprising:
(a) a silicone acrylate composition having a general formula:

wherein
- each $R^1$ is independently selected from hydrogen or methyl,
- each $R^2$ and $R^3$ is independently selected from, hydrogen alkyls, branched alkyls, methyl, ethyl, propyl, n-butyl, iso-butyl, tert-butyl, hexyl, 2-ethylhexyl, iso-octyl, iso-nonyl, iso-pentyl, tridecyl, stearyl, lauryl, and,
- each $R^4$ is a silane having the general formula wherein $R^5$ is selected from $-(CH_2)_3-NH-C(=O)-O-CH_2-CH_2-$, $-(CH_2)_3-NH-CH_2-CH(OH)-CH_2-$, and $-OCH_2-CH_2-$, and each $R^6$, $R^7$, and $R^8$ is independently selected from C1-C12 alkyl, phenyl, and $-(CH_2)_n-CH=CH_2$ where n is from 0 to 6, or wherein each R is a silsesquioxane having the general formula:

wherein $R^9$ is C1-12 alkyl,
$R^{10}$ is $-(CH_2)_z-$, where z is 3,
$R^{11}$ is selected from phenyl, C1-C12 alkyl, $-OH$, isopropoxy, and $-(CH_2)_n-CH=CH_2$ where n is between 0 and 6, and
$R^{12}$ is selected from C1-C12 alkyl,
wherein a is from 1 to 5 per R unit, q is from 1 to 300, t is 0, m is from 4-300, and the ratio of m/q is between 10/90 to 90/10,
wherein the composition includes between 0-99% w/w x groups, between 0-99% w/w y groups, 0% w/w s groups, and between 1-80% w/w r groups, where the % w/w of at least one of the x groups and the y groups is not zero;

(b) a silicone pressure sensitive adhesive; and
(c) an acrylic polymer that is different from the silicone acrylate composition of (a),
wherein the silicone acrylate blend composition lacks covalent bonds between the composition, the silicone pressure sensitive adhesive, and the acrylic polymer.

3. The silicone acrylate blend composition of claim 2, wherein the silicone pressure sensitive adhesive is selected from amine-compatible silicone adhesives and any combination thereof.

4. The silicone acrylate blend composition of claim 2, wherein the pressure sensitive adhesive has the general formula:

wherein $R^{13}$ is $-OH$, isopropoxy, or the combination thereof, and $R^{14}$ is C1-C12 alkyl wherein g is between 5-50 mol %, h is between 0.1-20 mol %, i is between 5-50 mol %, and d is between 5-90%, and wherein the weight ratio of (g+h+i)/d is between 10/90 to 90/10.

5. The silicone acrylate blend composition of claim 2, wherein the silicone pressure sensitive adhesive is (a) silanol-functional.

6. The silicone acrylate blend composition of claim 2, wherein the acrylic polymer is an acrylic polymer compound derived from methacrylic monomer, aliphatic acrylates, aliphatic methacrylates, cycloaliphatic acrylates, cycloaliphatic methacrylates, acrylamides, methacrylamides, hydroxy-functional (meth)acrylates, carboxy-functional (meth)acrylates, and any combination thereof, each having up to 20 carbon atoms in the alkyl radical.

7. The silicone acrylate blend composition of claim 6, wherein the acrylic polymer is derived from aliphatic acrylates selected from methyl acrylate, ethyl acrylate, propyl acrylate, n-butyl acrylate, iso-butyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and any combination thereof.

8. The silicone acrylate blend composition of claim 6, wherein the acrylic polymer is derived from aliphatic methacrylates selected from methyl methacrylate, ethyl methacrylate, propyl methacrylate, n-butyl methacrylate, iso-butyl methacrylate, tert-butyl methacrylate, hexyl methacrylate, 2-ethylhexyl methacrylate, iso-octyl methacrylate, iso-nonyl methacrylate, iso-pentyl methacrylate, tridecyl methacrylate, stearyl methacrylate, lauryl methacrylate, and any combination thereof.

9. A transdermal drug delivery system, comprising:
a silicone acrylate having a general formula:

wherein
- each $R^1$ is independently selected from hydrogen or methyl,
- each $R^2$ and $R^3$ is independently selected from hydrogen alkyls, branched alkyls, methyl, ethyl, propyl, n-butyl, iso-butyl, tert-butyl, hexyl, 2-ethylhexyl, iso-octyl, iso-nonyl, iso-pentyl, tridecyl, stearyl, lauryl, and, each $R^4$ is a silane having the general formula wherein $R^5$ is selected from —$(CH_2)_3$—NH—C(=O)—O—$CH_2$—$CH_2$—, —$(CH_2)_3$—NH—$CH_2$—CH(OH)—$CH_2$—, —$(CH_2)_3$— and —$OCH_2$—$CH_2$—, and each $R^6$, $R^7$, and $R^8$ is independently selected from C1-C12 alkyl, phenyl, and —$(CH_2)_n$—CH=$CH_2$ where n is from 0 to 6, or wherein each R is a silsesquioxane having the general formula:

$[(R^9)_2R^{10}SiO_{1/2}]_a[SiO_{4/2}]_q[R^{11}SiO_{3/2}]_t[(R^{12})_3SiO_{1/2}]_m$, wherein $R^9$ is C1-12 alkyl, $R^{10}$ is —$(CH_2)_z$—, where z is 3, $R^{11}$ is selected from phenyl, C1-C12 alkyl, —OH, isopropoxy, and —$(CH_2)_n$—CH=$CH_2$ where n is between 0 and 6, and $R^{12}$ is selected from C1-C12 alkyl, wherein a is from 1 to 5 per R unit, q is from 1 to 300, t is 0, m is from 4-300, and the ratio of m/q is between 10/90 to 90/10, wherein the composition includes between 0-99% w/w x groups, between 0-99% w/w y groups, 0% w/w s groups, and between 1-80% w/w r groups, where the % w/w of at least one of the x groups and the y groups is not zero;

an active agent for controlled transdermal delivery to a substrate;

optionally, one or more penetration enhancers; and optionally, one or more polymers configured to prevent crystallization of the active agent.

* * * * *